(12) United States Patent
Ritmiller et al.

(10) Patent No.: US 10,029,075 B2
(45) Date of Patent: Jul. 24, 2018

(54) SELF-CATHETERIZATION ASSISTANCE APPARATUS

(71) Applicants: Michael Ritmiller, Reisterstown, MD (US); John H Golden, Greensboro, GA (US); Eli B. Nichols, Durham, NC (US); David L. Foshee, Apex, NC (US)

(72) Inventors: Michael Ritmiller, Reisterstown, MD (US); John H Golden, Greensboro, GA (US); Eli B. Nichols, Durham, NC (US); David L. Foshee, Apex, NC (US)

(73) Assignee: MEDICAL TECHNOLOGIES OF GEORGIA, INC., Covington, GA (US)

( * ) Notice: Subject to any disclaimer, the term of this patent is extended or adjusted under 35 U.S.C. 154(b) by 440 days.

(21) Appl. No.: 14/629,050

(22) Filed: Feb. 23, 2015

(65) Prior Publication Data

US 2015/0238732 A1    Aug. 27, 2015

Related U.S. Application Data

(60) Provisional application No. 61/942,739, filed on Feb. 21, 2014.

(51) Int. Cl.
*A61M 25/01* (2006.01)
*A61M 25/02* (2006.01)

(52) U.S. Cl.
CPC ............ *A61M 25/02* (2013.01); *A61M 25/01* (2013.01); *A61M 2025/0177* (2013.01); *A61M 2025/024* (2013.01); *A61M 2025/0213* (2013.01); *A61M 2210/167* (2013.01)

(58) Field of Classification Search
CPC .............. A61M 25/01; A61M 25/02; A61M 2025/0213; A61M 2025/024; A61M 2210/167; A61M 2025/0177; A61M 2025/0206; A47G 23/0608; A47B 23/002; Y10S 128/26; A61B 5/6828; A61F 5/453
See application file for complete search history.

(56) References Cited

U.S. PATENT DOCUMENTS

| | | | | |
|---|---|---|---|---|
| 1,546,116 A | * | 7/1925 | Bradt | B41J 29/13 108/43 |
| 2,750,705 A | * | 6/1956 | Keveney | A01K 97/18 108/43 |
| 2,978,713 A | * | 4/1961 | Scalzitti | A61G 13/12 128/845 |
| 3,861,395 A | | 1/1975 | Taniguchi | |

(Continued)

OTHER PUBLICATIONS

"The Cath-Assist: A Self-Catheterization Assistive Device", (Speich et al) Apr. 24, 2015 (Apr. 24, 2015). Journal of Medical Devices, 9(2), see figure 1.

*Primary Examiner* — Adam Marcetich
(74) *Attorney, Agent, or Firm* — FisherBroyles LLP; Anthony J. DoVale

(57) ABSTRACT

A self-catheterization assistance apparatus is presented. The apparatus has a base, a penis retention element coupled to the base and a catheter retention member coupled to the base. A penis is inserted into and securedly attached to the penis retention element. A catheter housing is inserted into and securedly attached to the catheter retention member. An optional advancer advances the catheter through the catheter housing and into the penis.

22 Claims, 14 Drawing Sheets

(56) References Cited

U.S. PATENT DOCUMENTS

| | | | | |
|---|---|---|---|---|
| 3,924,631 | A * | 12/1975 | Mancusi, Jr. | A61B 17/122 128/DIG. 25 |
| 4,416,664 | A * | 11/1983 | Womack | A61M 25/02 604/174 |
| 5,176,274 | A * | 1/1993 | Jenkins | A47B 23/002 108/43 |
| 5,238,009 | A | 8/1993 | House | |
| 5,311,366 | A * | 5/1994 | Gerace | A61B 5/0079 248/476 |
| 5,752,933 | A | 5/1998 | Morrison | |
| 5,795,334 | A | 8/1998 | Cochrane, III | |
| 6,436,031 | B1 | 8/2002 | Salib | |
| 7,104,980 | B1 * | 9/2006 | Laherty | A61M 25/01 600/585 |
| 2006/0009742 | A1 * | 1/2006 | Solazzo | A61B 90/11 604/356 |
| 2007/0089646 | A1 * | 4/2007 | Duncan | A47B 23/002 108/43 |
| 2008/0223997 | A1 * | 9/2008 | Peterson | A47J 43/28 248/176.1 |
| 2010/0256580 | A1 * | 10/2010 | Faber | A61M 25/0017 604/329 |
| 2010/0269309 | A1 * | 10/2010 | Boesi | D06F 55/00 24/303 |
| 2011/0092928 | A1 * | 4/2011 | Saez | A61F 5/453 604/326 |
| 2012/0168571 | A1 * | 7/2012 | Bond | A61M 16/0488 248/70 |
| 2015/0062729 | A1 * | 3/2015 | Barbour | F16M 1/00 359/875 |

* cited by examiner

SELF-CATHETERIZATION ASSISTANCE APPARATUS

CROSS-REFERENCE TO RELATED APPLICATIONS

Continuity

This application claims priority to and the benefit of U.S. Provisional Patent Application No. 61/942,739, entitled SELF CATHETERIZATION ASSISTANCE APPARATUS, filed on Feb. 21, 2014, which is incorporated herein in its entirety by reference.

FIELD OF THE INVENTION

This invention relates generally to methods, devices and systems to aid a user in self-catheterization. More particularly this invention relates to methods, devices and systems that assists the user of a urinary catheter to advance it into a penis, with minimal need for user dexterity or personal grip strength.

BACKGROUND OF THE INVENTION

A wide variety of catheters is available for insertion into the body for introduction or withdrawal of fluids. Urinary catheters are flexible tubes designed to drain urine from the bladder by insertion into the urethra. They are packaged in sterile containers and can be lubricated for insertion prior to packaging or prior to use. Intermittent urinary catheters are designed to be inserted for each use and are commonly used by patients who are able to catheterize themselves.

Catheterization is accomplished by introducing the proximal tip of a catheter into the urethra, and then longitudinally collapsing and extending the pouch in an accordion-like manner until the tip reaches the bladder. The portion of the catheter remaining within the pouch is gripped between the walls of the pouch advanced out of the pouch through a catheter housing and into the urethra. During the pouch-extending phase, the catheter is held to resist a movement of the catheter back into the pouch by gripping the catheter between the pouch walls. The operation typically requires two hands to accomplish, as well as dexterity to make sure that the catheter does not retract back into the pouch. It is a difficult, if not impossible, activity for a quadriplegic, high paraplegic or person with low grip strength to accomplish.

Further, complications can make the process next to impossible, even for those with great dexterity or strength. For example, the fluid pressure from the bladder or the weight from the urine may tend to pull the lubricated catheter from the urethra and back into the urinary catheter pouch. To prevent this from occurring, the user must continuously grip the catheter until voiding is completed. Additionally, it can be difficult, if not impossible, for a quadriplegic, high paraplegic or person with low grip strength to hold the penis and the catheter housing while simultaneously inserting the catheter into the penis.

SUMMARY

Presented herein is a urinary catheter self-assistance apparatus, system and method for self-insertion of a urinary catheter. The catheter self-assistance apparatus can provide a means for a user to align and secure a penis and at least a portion of a catheter assembly, such as a catheter housing, a desired distance apart so that the catheter can be inserted by the user through the catheter housing and into the penis.

Generally, the self-catheterization assistance apparatus comprises a base, a penis retention element and a catheter retention member. In use, the user can position the penis on an upper surface of the base and can securely attach the penis to the base with the penis retention element. Similarly, the user can position the catheter pouch on the base such that the catheter housing is aligned with the penis and spaced a predetermined distance from the penis. The catheter housing can be securely attached to the base with the catheter retention member.

Related methods of operation are also provided. Other apparatuses, methods, systems, features, and advantages of the catheter self-assistance apparatus and the method of its use will be or become apparent to one with skill in the art upon examination of the following figures and detailed description. It is intended that all such additional apparatuses, methods, systems, features, and advantages be included within this description, be within the scope of the catheter self-assistance apparatus and the method of its use, and be protected by the accompanying claims.

DESCRIPTION OF THE FIGURES

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

DESCRIPTION OF THE INVENTION

Figure 1:
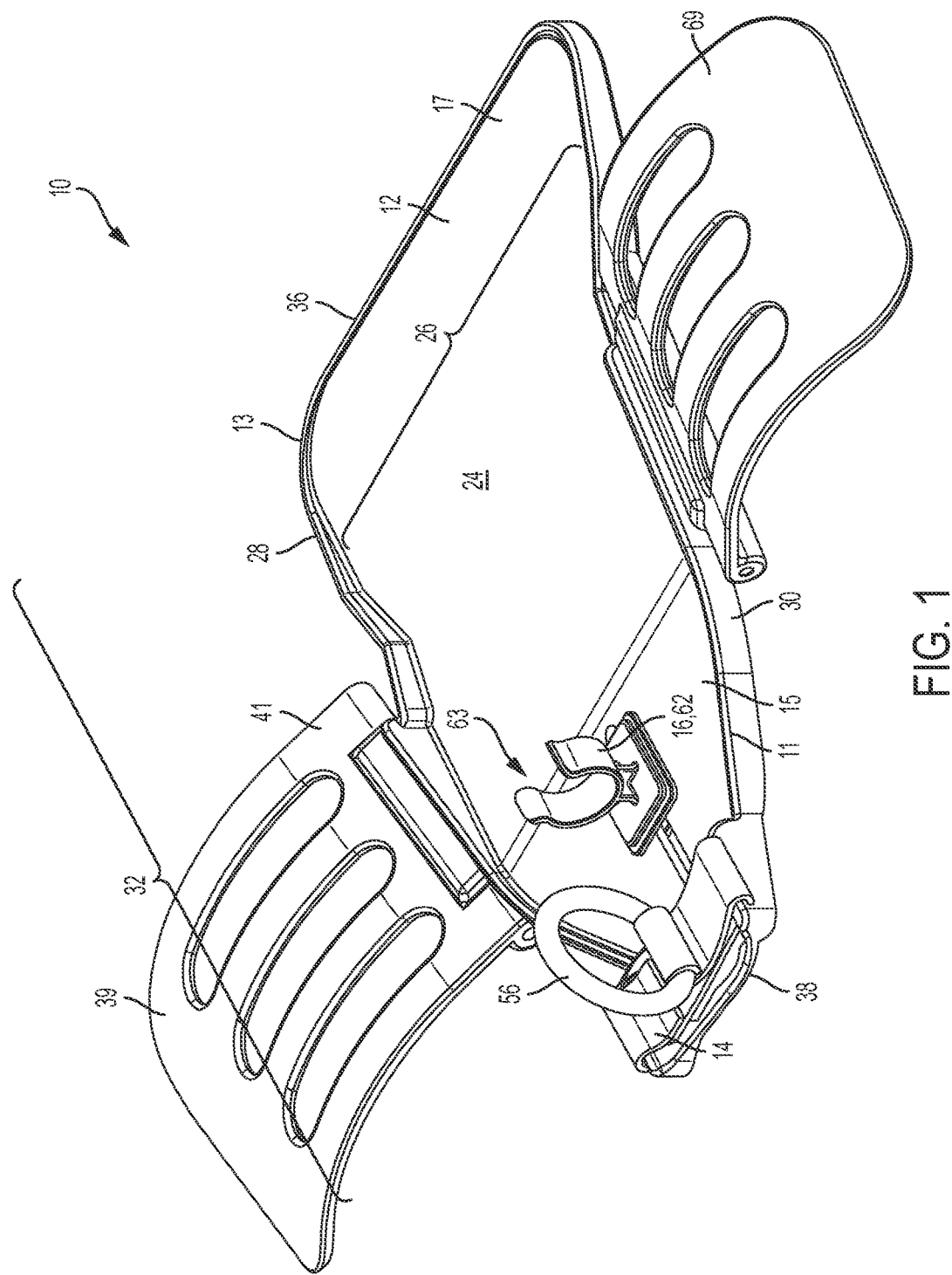
FIG. 1 is a perspective view of a self-catheterization assistance apparatus of the present application, according to one aspect, showing a base, a penis retention element, and a catheter retention member.
Figure 2:
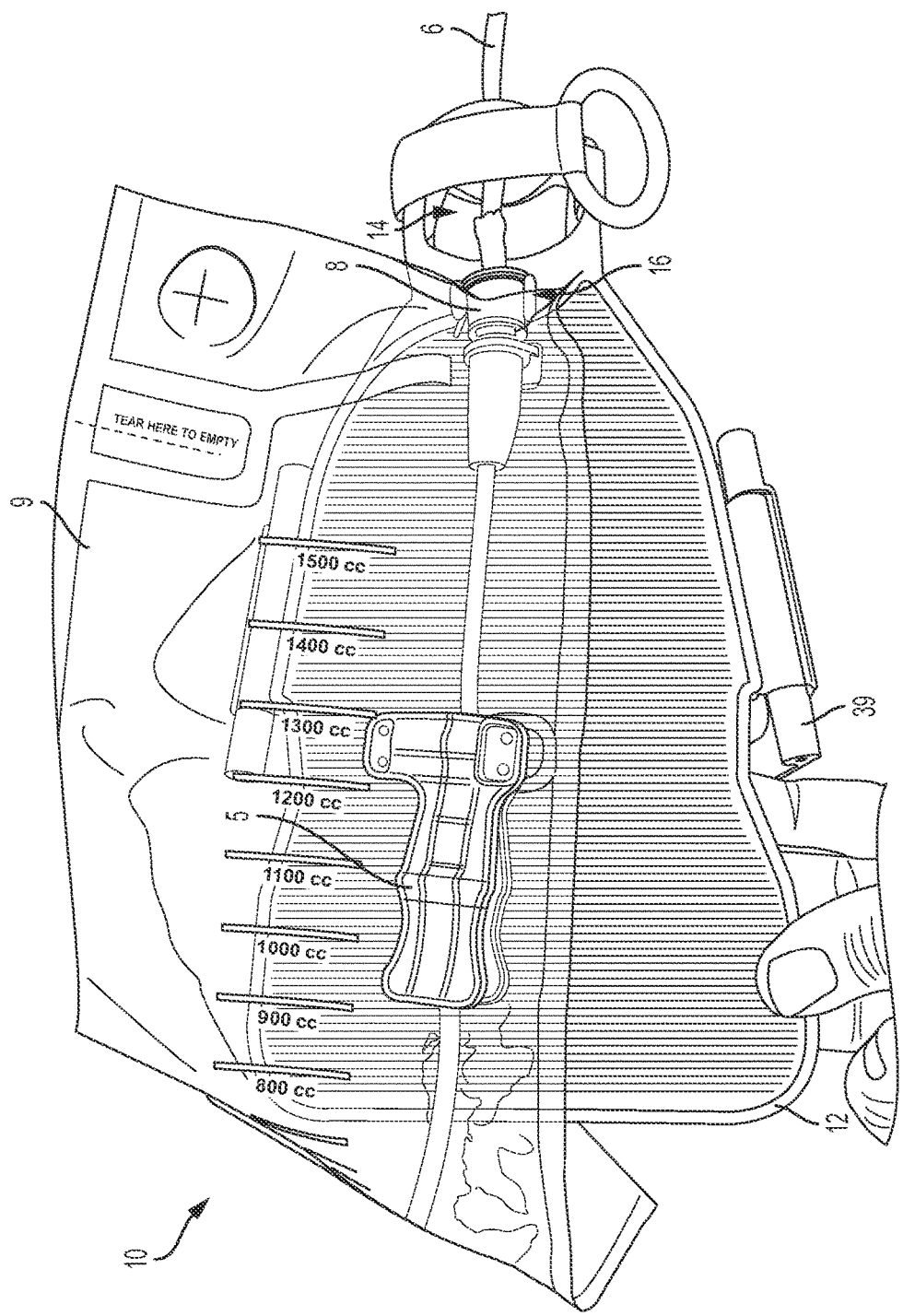
FIG. 2 is a perspective view of the self-catheterization assistance apparatus of FIG. 1, showing a catheter assembly positioned on the apparatus, according to one aspect.

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "strap" includes aspects having two or more straps unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Terms used herein, such as "exemplary" or "exemplified," are not meant to show preference, but rather to explain that the aspect discussed thereafter is merely one example of the aspect presented.

The term "substantially," as used herein, may be applied to modify any quantitative representation that could permissibly vary without resulting in a change in the basic function to which it is related.

Presented herein is a self-catheterization assistance apparatus and method of use. In one aspect and as illustrated in FIGS. 1-5, the self-catheterization assistance apparatus 10 comprises at least a base 12, a penis retention element 14 and a catheter retention member 16. Optionally, the self-catheterization assistance apparatus can further comprise an advancer 18 as described below with regard to FIGS. 3, 6-7.

The base 12 can have a lower surface 22 and an opposed upper surface 24 configured to support at least a portion of a penis of a user and at least a portion of a catheter, according to one aspect. At least a portion of the base can be a substantially planar base. The base 12 can have a base width 26 extending from a first side 28 of the base to a second side 30. In another aspect, the base 12 can have a longitudinal base length 32 extending along a longitudinal axis $L_A$ from a distal edge 36 of the base to a proximal edge 38. In another aspect, the base width can be substantially the same at the distal and the proximal edges of the base 12. Optionally, in one aspect, the proximal edge 38 of the base can have a base width 26 that is less than the base width of the distal edge 36 and/or a central portion 40 of the base 12. In still another aspect, a lip 11 can be formed around at least a portion of a perimeter edge 13 of the base. The lip can prevent or restrict objects from rolling or flowing off the perimeter edge of the base 12.

In another aspect, at least a first portion 15 of the base 12 can be positioned in a first plane, a second portion 17 of the base can be positioned in a second plane that is at a base acute angle relative to the first plane, and the base 12 angled or curved to join portions 15, 17. For example, the penis retention element 14 can be positioned in the first plane, and the distal edge 36 of the base can be positioned in the second plane. In another aspect, the base acute angle can be about one degree, about two degrees, about four degrees, about six degrees, about eight degrees, about ten degrees, about twelve degrees, about fourteen degrees, about sixteen degrees, about eighteen degrees, about twenty degrees, about twenty-five degrees, about thirty degrees, about thirty-five degrees, about forty degrees, about forty-five degrees, or greater than about forty-five degrees. In use, described more fully below, the base acute angle can be selected so that urine flows downwardly from the penis and into a catheter pouch 9.

In one aspect, at least a portion of the first side 28 of the base 12 can extend substantially normal to the distal edge 36 of the base. For example, a portion of the first side of the base 12 can extend substantially normal to the distal edge of the base and a portion of the first side 28 of the base 12 can taper inwardly towards the second side 30 of the base. Similarly, at least a portion of the second side of the base 12 can extend substantially normal to the distal edge 36 of the base. In another example, a portion of the second side of the base 12 can extend substantially normal to the distal edge 36 of the base, and a portion of the second side 30 of the base 12 can taper inwardly towards the first side of the base. In one aspect, the proximal edge 38 of the base can be sized and shaped to fit between a portion of the legs of the user, and at least a portion of the first side 28 and/or the second side 30 of the base can be configured to be grasped by the legs of the user. That is, at least a portion of the first side and/or the second side of the base 12 can be sized and shaped so that the base can be squeezeably grasped between a portion of the legs of the user. For example, at least a portion of the first side 28 and the second side 30 can be arcuate in shape to conform to shape of the legs of the user.

The base can further comprise a plurality of stabilizers 39, according to one aspect. The stabilizers can extend away from the base 12 a predetermined distance to assist the user in positioning and/or grasping the apparatus with his legs, according to one aspect. For example, a first stabilizer can extend from the first side 28 of the base, and a second stabilizer can extend from the second side 30 of the base. In another aspect, at least a portion of the stabilizers 39 can be curved to conform to the shape of the top of the legs of the user. In another aspect, each stabilizer of the plurality of stabilizers 39 can be rotatable about and between a first stabilizer position, in which a proximal portion 41 of the stabilizer is substantially parallel to the upper surface 24 and/or the first plane of the base 12, and a second stabilizer position in which the proximal portion of the stabilizer is substantially normal to the upper surface and/or the first plane of the base. In a further aspect, each stabilizer of the plurality of stabilizers 39 can be fixedly secured in any position about and between the first stabilizer position and the second stabilizer position. That is, each stabilizer can lock or be secured in a desired stabilizer position.

In one aspect, at least a portion of the proximal edge 38 of the base 12 can be curved to conform to the shape of a portion of the penis of the user. Optionally, at least a portion of the proximal edge can be substantially linear. In another aspect, a penis cavity 42 can be defined in the upper surface 24 of the base 12 configured to hold at least a portion of a penis of the user (see FIG. 3). In this aspect, the penis cavity can extend from a first cavity position 44 at the proximal edge of the base longitudinally towards the distal edge 36 of the base to a second cavity position 46. In another aspect, the depth of the penis cavity with respect to the upper surface can decrease as the cavity extends towards the distal edge. That is, the depth of the penis cavity at the first cavity position 44 can be greater than the penis cavity 42 depth at the second cavity position 46.

In one aspect, a catheter housing chamber 48 (FIG. 3) can be defined in the upper surface 24 of the base 12 configured to hold at least a portion of a catheter housing. In this aspect, the catheter housing chamber 48 can be spaced from the second cavity position 46 a predetermined distance. In another aspect, the depth of the catheter housing chamber 48 with respect to the upper surface can be substantially constant at all locations in the chamber. Optionally, portions of the catheter housing chamber can be deeper or shallower than other portions to accommodate the catheter housing.

The penis retention element 14 can define a penis opening sized and shaped such that at least a portion of the penis of the user can be inserted therethrough. In one aspect, the penis retention element can be coupled to the upper surface 24 of the base 12. In another aspect, the penis retention element 14 can be coupled to the upper surface of the base adjacent the proximal edge 38 of the base. Optionally, the penis retention element 14 can be spaced from the proximal edge of the base 12 a first predetermined distance. In another aspect, the penis retention element 14 can overlie at least a portion of the penis cavity 42.

Optionally, the penis retention element 14 can be a stationary penis retention element or a selectively adjustable penis retention element. In one aspect, the penis retention element 14 can be a flexible, selectively adjustable element formed from a strap, band and the like, or a rigid element formed from a housing and the like. For example, a flexible penis retention element can comprise hook and loop fastening straps. In this example, a hook portion 50 of the penis retention element 14 can be coupled to the base 12 adjacent the first side 28 or the second side 30 of the base, and a loop portion 52 of the penis retention element can be coupled to the base adjacent to the opposed first side or the second side. The loop portion can extend over at least a portion of the penis cavity 42 for selective coupling with the hook portion of the penis retention element 14. The flexible penis retention element can have a selectively adjustable inner diameter (i.e., the diameter of the penis opening) to accommodate penises having different diameters and/or to selectively apply more or less pressure to a penis inserted therethrough.

In another example, a rigid penis retention element 14 can be formed from a sleeve 54 (FIG. 4) having a fixed inner diameter sized and shaped such that the penis of the user can be inserted therethrough. Optionally, the rigid penis retention element 14 can be formed from a sleeve having a selectively adjustable inner diameter to accommodate penises having different diameters and/or to selectively apply more or less pressure to a penis inserted therethrough.

Figure 14:
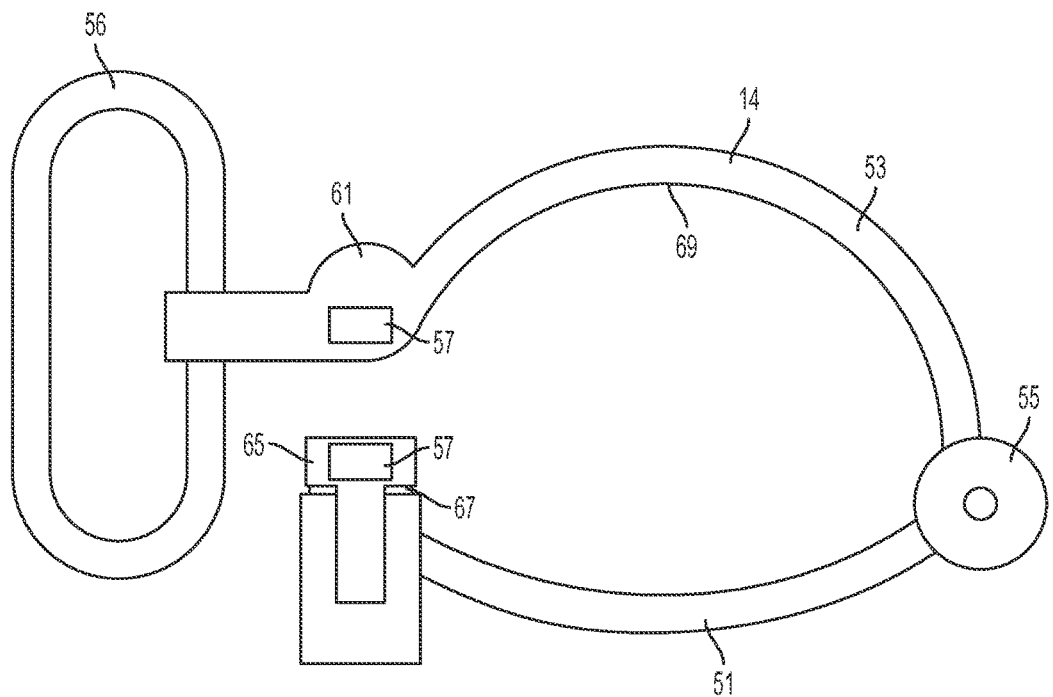
FIG. 14 is a cross-sectional view of a hinged penis retention element of the self-catheterization assistance apparatus of the present application in an open position, according to one aspect.
Figure 15:
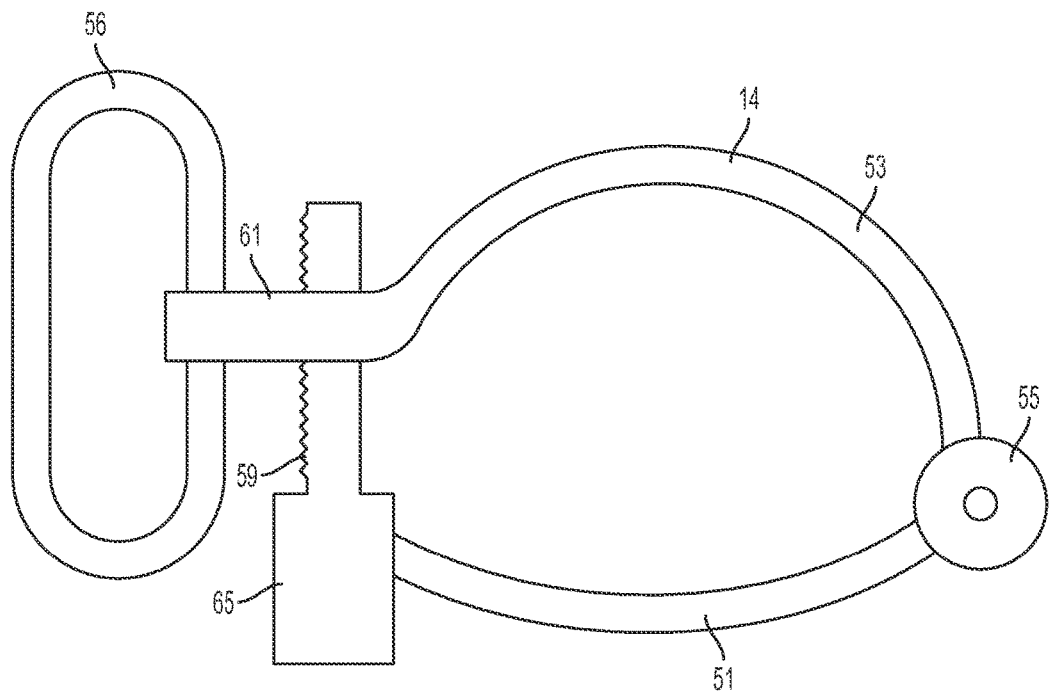
FIG. 15 is an elevational view of a hinged penis retention element of the self-catheterization assistance apparatus of the present application in a closed position, according to one aspect.

In one aspect, the penis retention element 14 can be a hinged penis retention element, as illustrated in FIGS. 14 and 15. In this aspect, the hinged penis retention element can comprise a hinge 55 positioned between a first arm 51 and a second arm 53 such that the second arm can rotate relative to the first arm. For example, the second arm can rotate about and between a first, closed position, in which a distal end 61 of the second arm 53 is in contact with a portion of a distal end 65 of the first arm 51, and a second, open position in which the distal end 61 of the second arm is spaced from the distal end 65 of the first arm 51 a predetermined distance. In another aspect, a portion of the first arm 51 can be coupled to the upper surface 24 of the base 12. In a further aspect, the hinged penis retention element can have a selectively adjustable inner diameter (i.e., the diameter of the penis opening) to accommodate penises having different diameters and/or to selectively apply more or less pressure to a penis inserted therethrough.

The penis retention element 14 can further comprise a means for securely attaching the second arm 53 in the closed position. In one aspect, the means for securely attaching the second arm in the closed position comprises at least one magnet 57 positioned on a portion of the distal end 65 of the first arm 51, and a complementary magnet positioned on a portion of the distal end 61 of the second arm 53. The magnet of each arm can attract each other to maintain the second arm in the closed position. In another aspect, at least one washer 67 or other spacer can be positioned on the distal end of the first and/or the second arm to adjust the diameter of the penis retention element (i.e., the penis opening) in order to accommodate penises of different sizes. For example, a plurality of washers can be positioned beneath the magnet 57 of the first arm 51 to increase the diameter of the penis opening.

In a further aspect, the means for securely attaching the second arm 53 in the closed position can comprise a ratcheting system 59. In this aspect, a plurality of ridges or notches can be defined in a portion of the distal end 65 of the first arm 51 and a plurality of mating ridges or notches can be defined in a portion of the distal end 61 of the second arm 53. In use, the ridges of each arm can engage the ridges of the opposed arm to maintain the second arm 53 in the closed position. As can be appreciated, the position of the second arm relative to the first arm 51 can be adjusted to accommodate penises of different sizes by the ridges of the second arm 53 engaging different ridges of the first arm.

In one aspect, the penis retention element 14 can further comprise a retention element grasping loop 56. In this aspect, the retention element grasping loop can be coupled to a portion of a selectively adjustable penis retention element so that the penis retention element can be easily adjusted by the user. For example, if the penis retention element 14 comprises a hook and loop fastener, as described above, the retention element grasping loop 56 can be coupled to the loop portion 52 of the hook and loop fastener so that the user can selectively adjust the position and/or tension in the fastener by inserting at least one finger through the retention element grasping loop. As can be appreciated, the retention element grasping loop 56 can be coupled to any portion of a penis retention element 14 that is adjustable. For example, the retention element grasping loop 56 can be coupled to the second arm 53 to easily allow for adjustment of the second arm about and between the closed position and the open position.

In one aspect, at least a portion of an inner surface of the penis retention element 14 can be covered with a cushioning material 69 for the comfort of the user and/or to accommodate penises having different sizes. For example, at least a portion of an inner surface of the second arm 53 can have a soft foam applied thereto. In another aspect, the cushioning material can be replaceable for cleaning.

The catheter retention member 16 can define a catheter opening sized and shaped such that at least a portion of a catheter can be inserted therein. In one aspect, the catheter retention member can be coupled to the upper surface 24 of the base 12. In another aspect, the catheter retention member can be spaced from the proximal edge 38 of the base 12 a second predetermined distance that is greater than the first predetermined distance. Optionally, the second predetermined distance can be selectively adjustable. That is, the catheter retention member 16 can slide substantially longitudinally (in the direction of the longitudinal axis $L_A$ of the base) about and between a first member position and a second member position that is further away from the proximal edge of the base 12 than the first member position. For example, a longitudinal slot can be defined in a portion of the base 12, so that a tab of the catheter retention member can slidingly engage the slot. In yet another aspect, the catheter retention member 16 can overlie at least a portion of the catheter housing chamber 48. The catheter retention member 16 and the penis retention element 14 can be substantially aligned longitudinally so that in use, described more fully below, the catheter can be substantially aligned with the penis of the user.

In one aspect, the catheter retention member 16 can be a fixed catheter retention member or a selectively adjustable catheter retention member. In another aspect, the catheter retention member 16 can be a flexible, selectively adjustable member formed from a strap, band and the like, or a rigid member formed from a housing and the like. For example, a flexible catheter retention member can comprise a hook and loop fastener. In this example, a hook portion 58 of the catheter retention member 16 can be coupled to the base 12 adjacent the first side 24 or the second side 26 of the base, and a loop portion 60 of the catheter retention member can be coupled to the base adjacent to the opposed first side or the second side. The loop portion can extend over at least a portion of the catheter housing chamber 48 for selective coupling with the hook portion of the catheter retention member 16.

In another example, a rigid catheter retention member 16 can be formed from a frame 62 having a fixed inner diameter (that is, the diameter of the catheter opening) sized and shaped such that the catheter housing 8 can be inserted therein. For example, the frame can be substantially "C"-shaped, substantially "U"-shaped and the like. In one aspect, the frame 62 can define a gap 63 therein so that the catheter housing can be inserted through the gap into the rigid catheter retention member 16. In a further aspect, the rigid catheter member can be outwardly biased as the catheter housing in inserted through the gap so that upon the catheter housing 8 being positioned in the gap, the catheter member returns to its original size and shape. Optionally, the rigid catheter retention member can be formed from a frame having a selectively adjustable inner diameter to accommodate catheter housings having different diameters and/or to selectively apply more or less pressure to a catheter housing 8 inserted therein.

The frame 62 of the catheter retention member 16 can be spaced from the upper surface 24 of the base 12 a predetermined frame height. In one aspect, the frame height can be selectively adjustable. For example, at least one washer and/or spacer can be positioned between the frame and the base so that the frame 62 is spaced a desired frame height from the base 12.

Figure 5:
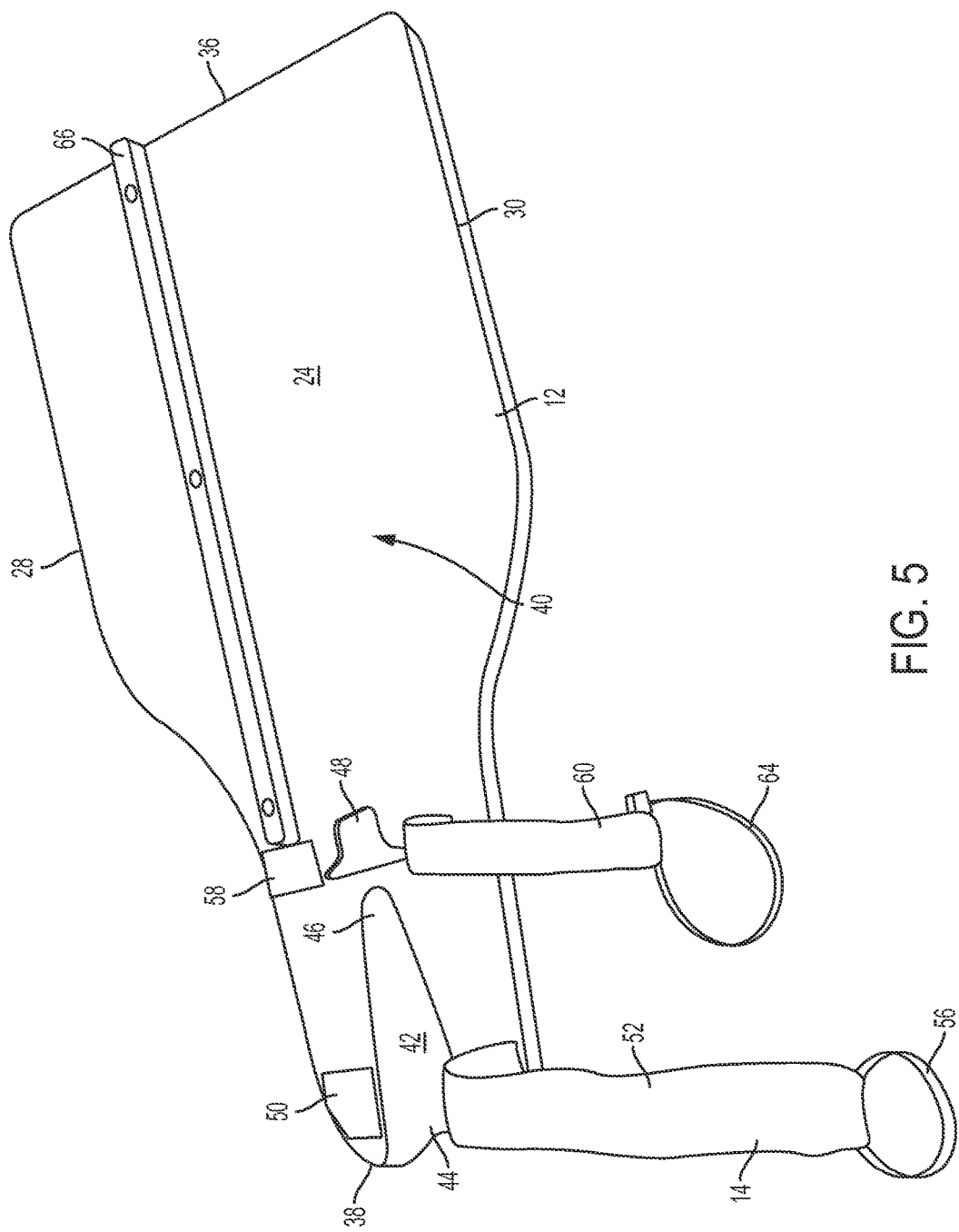
FIG. 5 is a perspective view of the self-catheterization assistance apparatus of FIG. 3, according to one aspect.

In one aspect, the catheter retention member 16 can further comprise a catheter member grasping loop 64 (see FIG. 5). In this aspect, the catheter member grasping loop can be coupled to a portion of a selectively adjustable catheter retention member 16 so that the catheter retention member can be easily adjusted by the user. For example, if the catheter retention member 16 comprises a hook and loop fastener, as described above, the catheter member grasping loop 64 can be coupled to the loop portion 60 of the hook and loop fastener so that the user can selectively adjust the positioned and/or tension in the fastener by inserting at least one finger through the grasping loop. As can be appreciated, the catheter member grasping loop 64 can be coupled to any portion of a catheter retention member 16 that is adjustable.

The base 12 can further comprise a guide rail 66 (FIG. 5), according to one aspect, configured to matingly engage a slot 68 formed in the advancer 18, described more fully below. The guide rail can be coupled to or formed integrally with the upper surface 24 of the base and can extend upwards away from the upper surface of the base such that the slot of the advancer can slide along at least a portion of the guide rail 66. In another aspect, the guide rail can be substantially parallel to the longitudinal axis of the base. In a further aspect, the guide rail 66 can be spaced from the first side 28 and/or the second side 30 of the base 12 a third predetermined distance. Thus, the guide rail 66 can be positioned closer to the first side of the base than the second side, or alternatively, the guide rail 66 can be positioned closer to the second side 30 of the base 12 than the first side 28. In still another aspect, the guide rail 66 can extend from the distal edge 36 of the base 24 to a position adjacent the catheter retention member 16. Optionally, the guide rail 66 can be spaced from the distal edge of the base 24 and/or the catheter retention member 16.

As can be appreciated, in one aspect, the guide rail 66 can comprise any means configured to provide sliding engagement between the base 12 and the advancer 18. For example, the guide rail can comprise a groove defined in the upper surface 24 of the base configured to matingly engage a leg coupled to or formed with the advancer.

Figure 3:
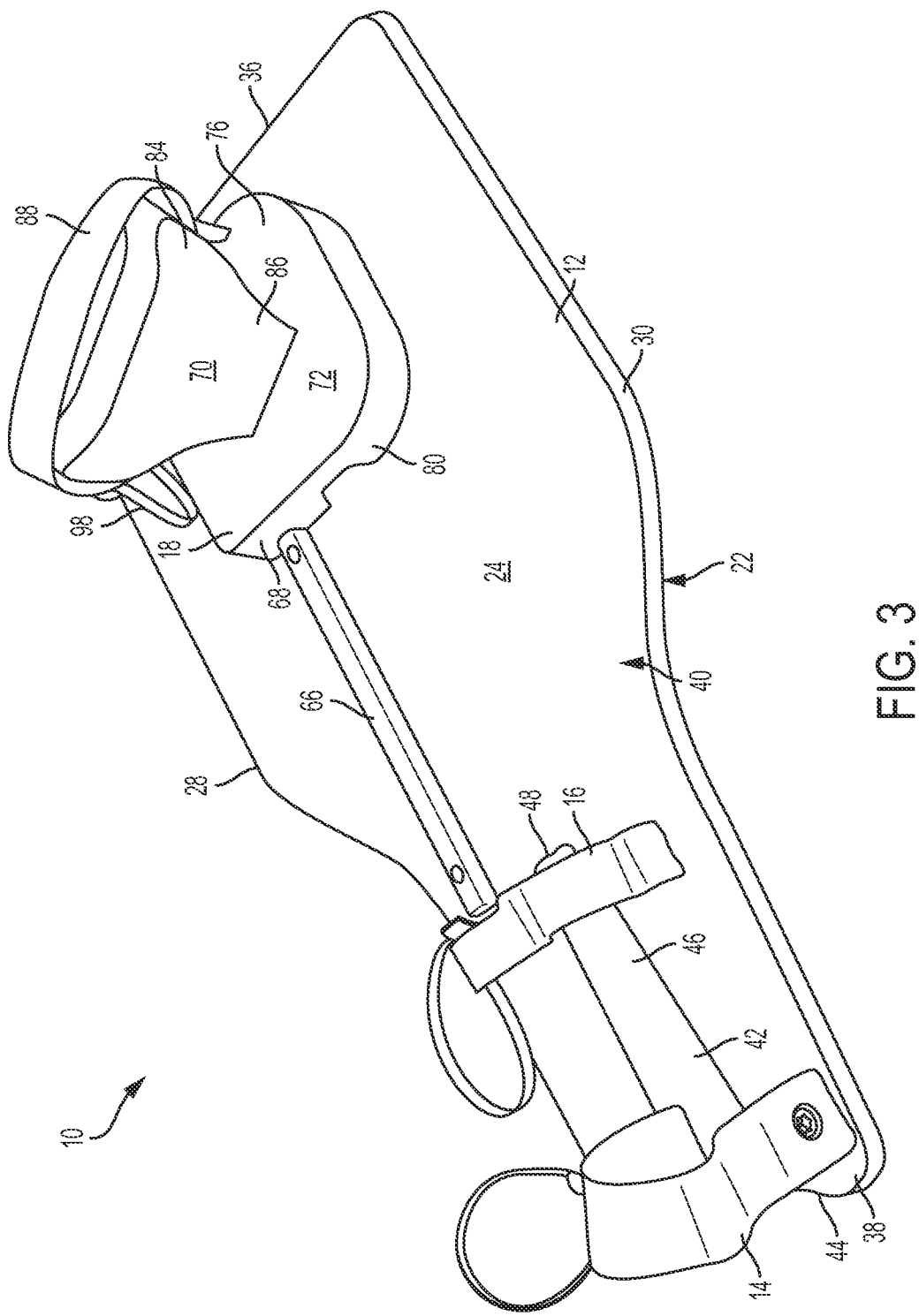
FIG. 3 is a perspective view of a self-catheterization assistance apparatus of the present application, according to one aspect, showing a base, a flexible penis retention element, a catheter retention member and an advancer.
Figure 4:
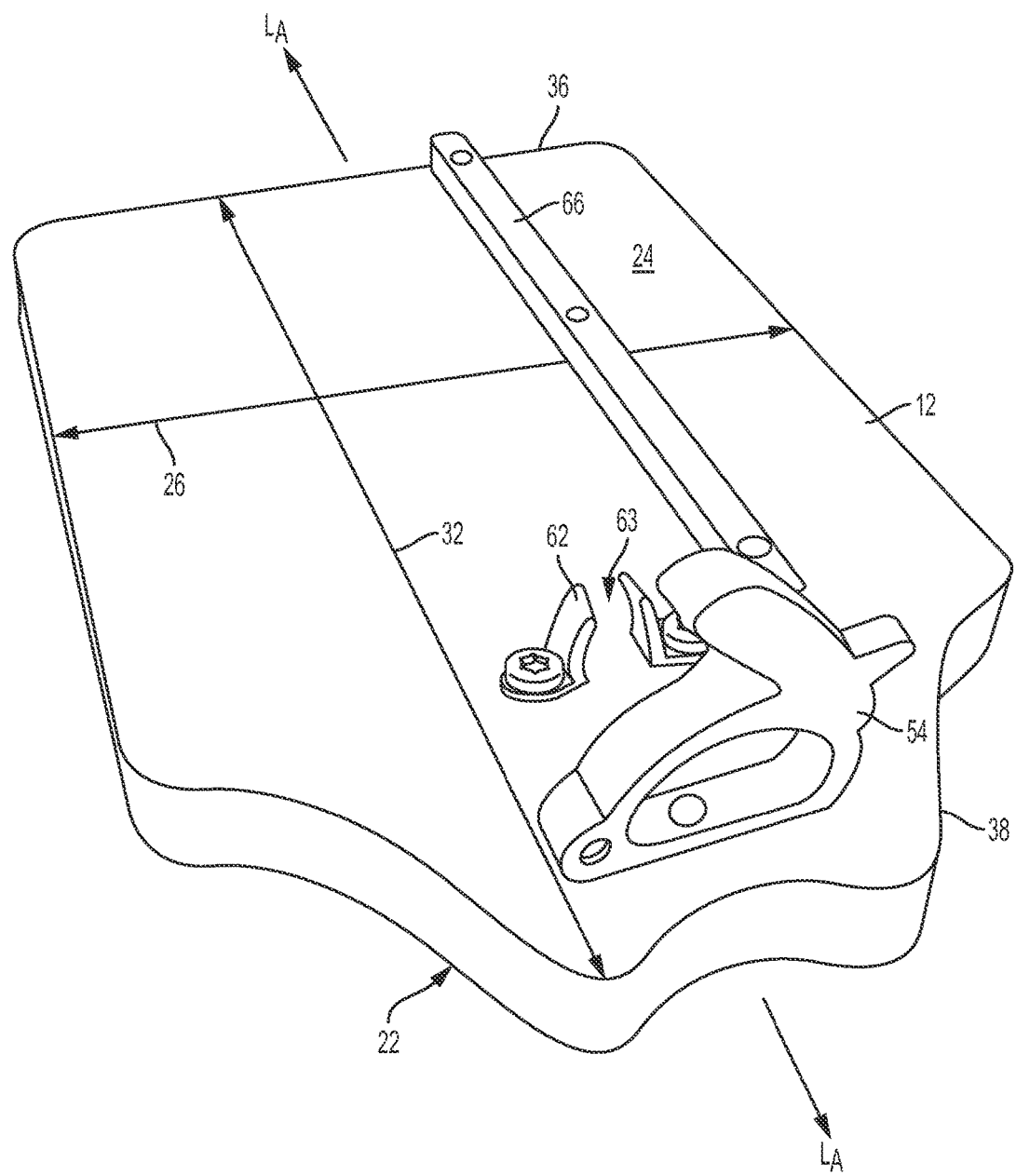
FIG. 4 is perspective view of a self-catheterization assistance apparatus of the present application, according to one aspect, showing a base, a substantially rigid penis retention element and a catheter retention member.
Figure 6:
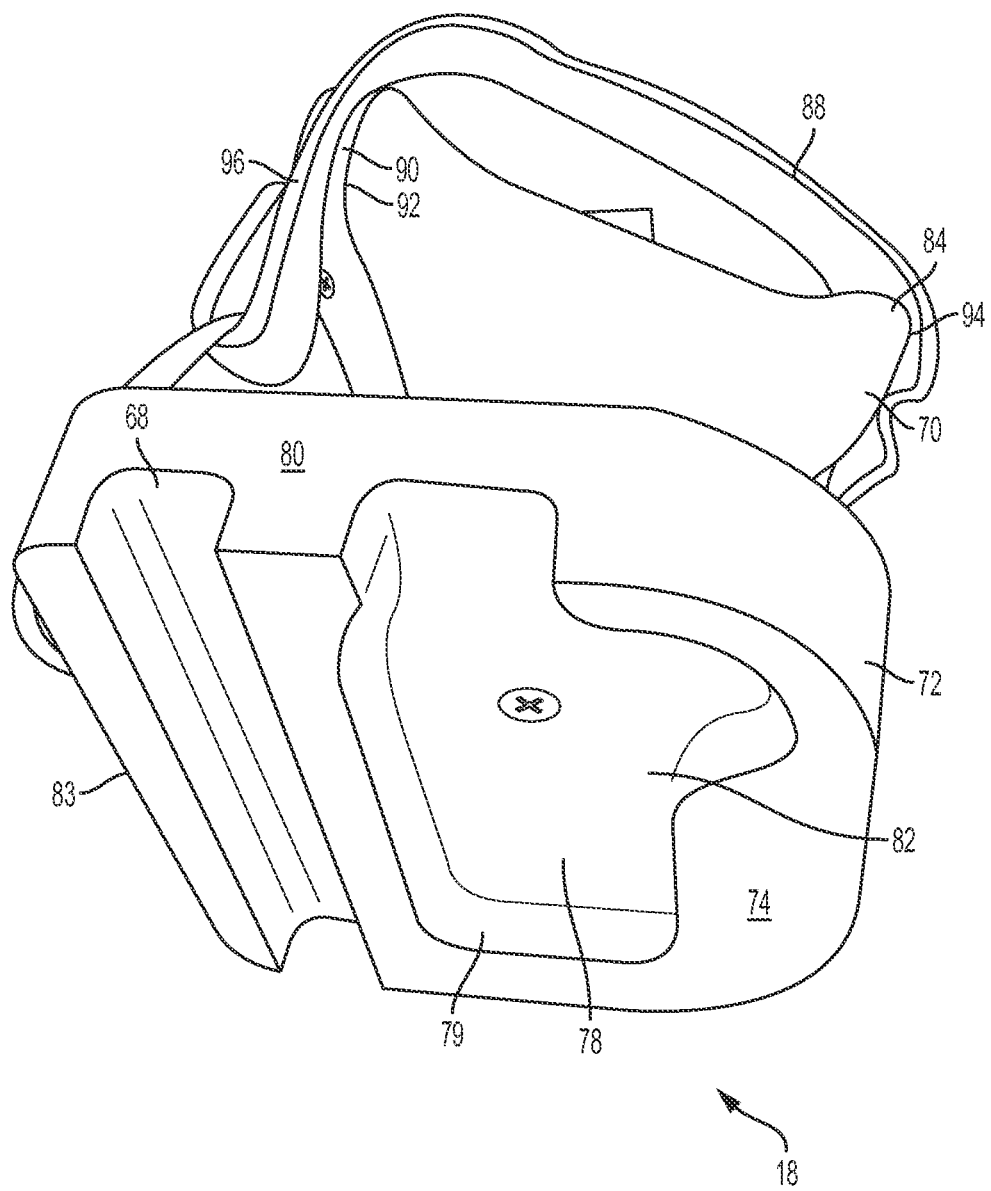
FIG. 6 is a perspective view of the advancer of the self-catheterization assistance apparatus of FIG. 3, according to one aspect.
Figure 7:
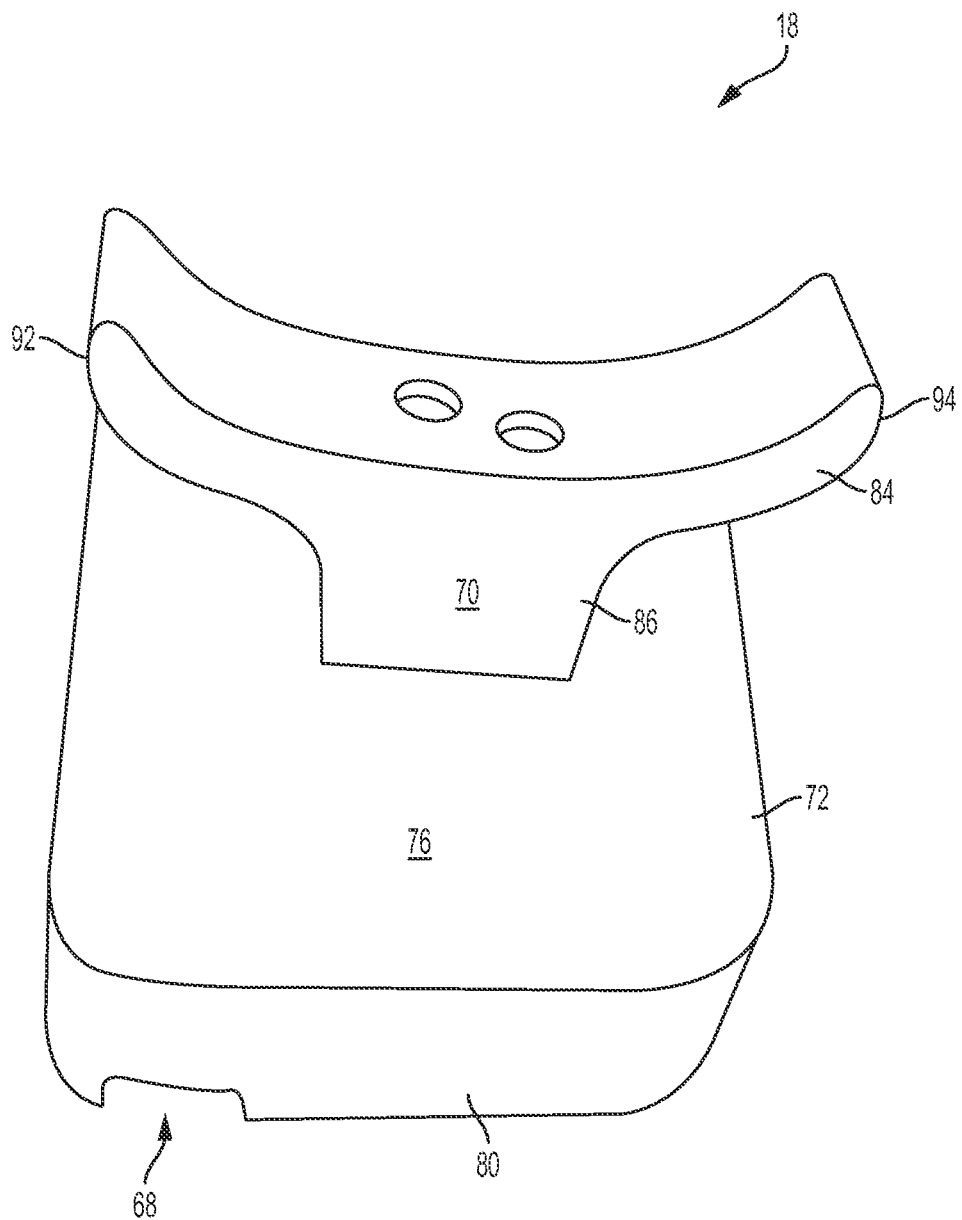
FIG. 7 is a perspective view of an advancer of the self-catheterization assistance apparatus of the present application, according to one aspect.
Figure 8:
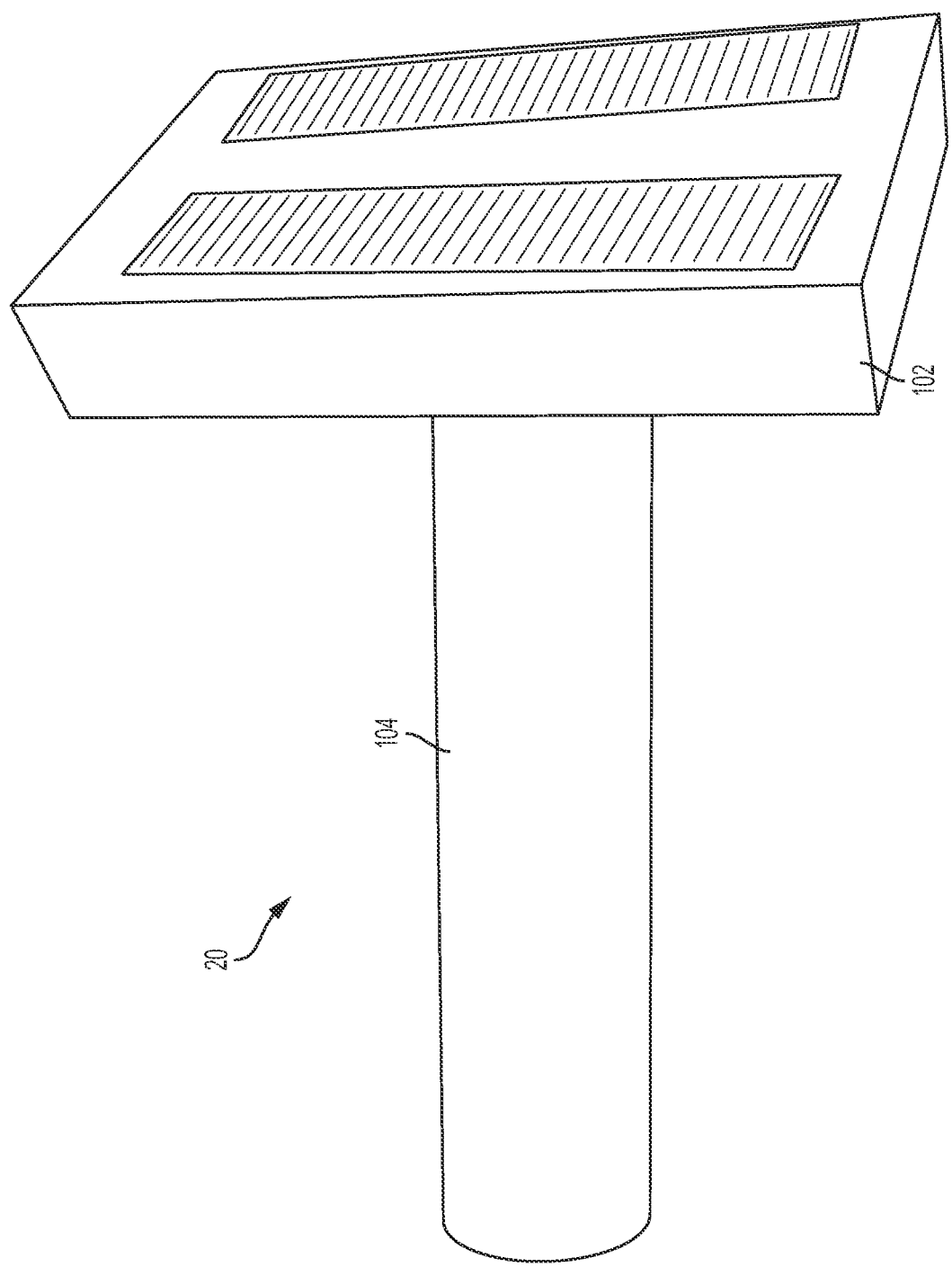
FIG. 8 is a perspective view of a holder of the self-catheterization assistance apparatus of the present application, according to one aspect.
Figure 9:
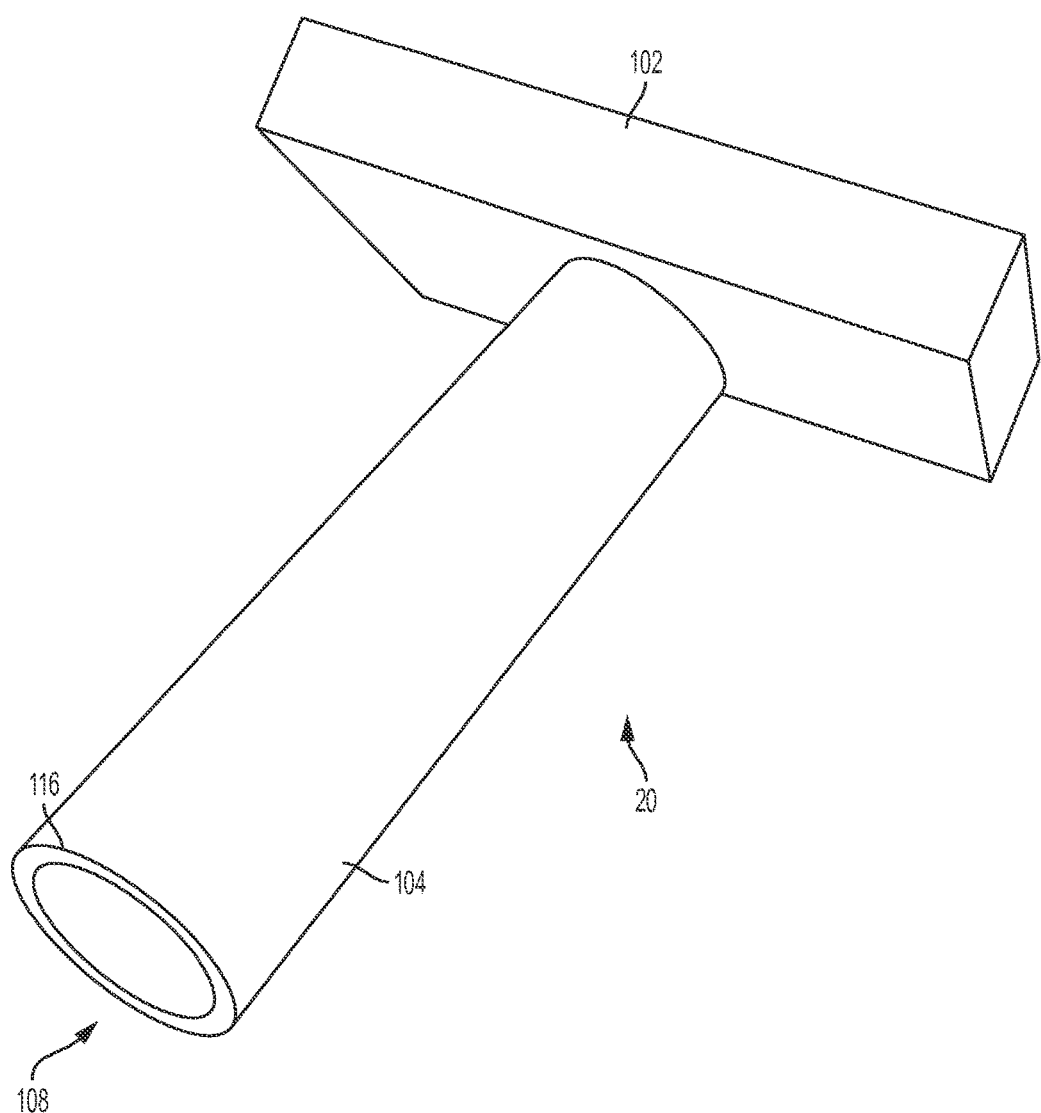
FIG. 9 is a perspective view of the holder of FIG. 8.
Figure 10:
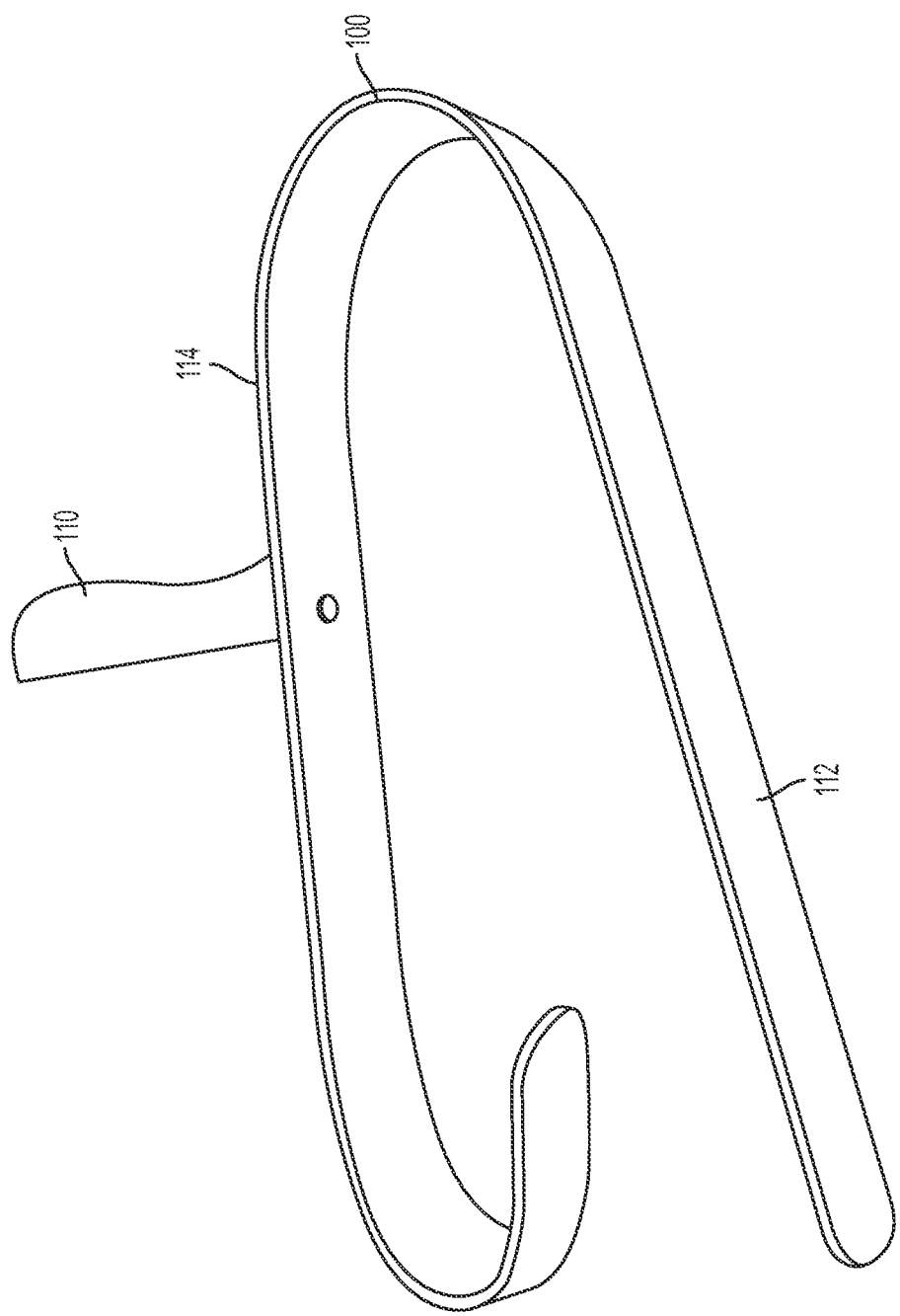
FIG. 10 is a perspective view of a hook of the self-catheterization assistance apparatus of the present application, according to one aspect.

Referring now to FIGS. 3, 6 and 7, the advancer 18 is configured to assist the user in advancing the catheter toward the user. In one aspect, the advancer comprises a handle 70 and a platform 72. The platform has a bottom surface 74 configured to slide on the upper surface 24 of the base 12, and an opposed top surface 76 configured to support the handle. In one aspect, the bottom surface and/or the upper surface of the platform can be substantially planar. In another aspect, a catheter gripping cavity 78 can be defined in a portion of the bottom surface. In this aspect, the catheter gripping cavity can have at least one sidewall 79 and can be sized and shaped to at least partially contain a catheter gripping means therein. For example, if the catheter gripping means comprises a catheter gripper assembly 5 as described in U.S. Pat. No. 7,632,256, the catheter gripping cavity 78 can be sized and shaped so that at least a portion of the catheter gripping assembly can be contained therein. In this manner, as the platform 72 is moved, the at least one sidewall of the catheter gripping cavity can contact a portion of the catheter gripping assembly, and the sidewall can urge the catheter gripping assembly to move in the direction of movement of the platform 72. In another aspect, the catheter gripping cavity 78 can extend from a front edge 80 of the platform to a central portion 82 of the platform.

As discussed above, a slot 68 can be defined in a portion of the bottom surface 74 of the advancer 18 configured to engage the guide rail 66 of the base 12. In one aspect, the slot can be substantially linear. In another aspect, the slot 68 can be spaced from an outer side edge 83 of the platform 72 such that when the guide rail of the base is matingly engaged with the slot, a catheter gripping assembly positioned in the catheter gripping cavity 78 can be substantially longitudinally aligned with the catheter retention member 16 and/or the penis retention element 14. In another aspect, the slot 68 can extend longitudinally from the front edge 80 of the platform to a rear edge.

The handle 70 can be coupled to or formed integrally with the top surface 76 of the platform 72. In one aspect, the handle can extend upwards from the platform such that when in use, as described below, a longitudinal axis of the handle is substantially normal to the longitudinal axis of the base 12. In another aspect, the handle can be sized and shaped to provide a convenient and easy to grasp device for the user. For example, the handle can have an arcuate upper member 84 configured to engage the hand of the user. In another example, a lower member 86 of the handle can have a smaller width than the upper member so that the fingers of the user can easily grasp or otherwise engage the lower member and/or portions of the upper member of the handle 70.

In one aspect, the handle 70 can comprise a hand retention element 88 configured to selectively attach the hand of the user to the handle. The hand retention element can be a stationary hand retention element or, alternatively, a selectively adjustable hand retention element. In this aspect, the hand retention element 88 can be a flexible element formed from a strap, band and the like, or a rigid element formed from a housing and the like. For example, a flexible hand retention element can comprise a hook and loop fastener. In this example, a hook portion 90 of the hand retention element 88 can be coupled to a first side 92 or a second side 94 of the handle 70, and a loop portion 96 of the hand retention element can be coupled to the opposed first side or the second side. The loop portion can extend over at least a portion of the handle for selective coupling with the hook portion of the hand retention element 88.

In another example, a rigid hand retention element 88 can be formed from a sleeve having a fixed inner diameter sized and shaped such that the at least a portion of the hand of the user can be inserted therethrough. Optionally, the rigid hand retention element 88 can be formed from a sleeve having a selectively adjustable inner diameter to accommodate hand having different sizes and/or to selectively apply more or less pressure to a hand inserted therethrough.

In one aspect, the hand retention element 88 can further comprise a hand retention element grasping loop 98. In this aspect, the hand retention element grasping loop can be coupled to a portion of a selectively adjustable hand retention element so that the hand retention element can be easily adjusted by the user. For example, if the hand retention element 88 comprises a hook and loop fastener, as described above, the hand retention element grasping loop 98 can be coupled to the loop portion 96 of the hook and loop fastener so that the user can selectively adjust the positioned and/or tension in the fastener by inserting at least one finger through the hand retention element grasping loop. As can be appreciated, the hand retention element grasping loop 98 can be coupled to any portion of a hand retention element 88 that is adjustable.

Optionally, the self-catheterization assistance apparatus 10 can further comprise a means for detachably securing the apparatus to a bed and/or chair of the user. In one aspect, the means for detachably securing the apparatus 10 to a bed and/or chair of the user can comprise detachably securing the base 12 to the bed and/or chair of the user. For example, the self-catheterization assistance apparatus 10 can further comprise at least one of a holder 20 and a hook 100, illustrated in FIGS. 8-13.

In one aspect, the holder 20 can comprise a mounting plate 102 and a holding finger 104 extending therefrom. The mounting plate can be configured to couple to the lower surface 22 of the base 12 by selective coupling of a mounting surface 106 of the mounting plate to the lower surface of the base. For example, at least a portion of the mounting surface and the lower surface of the base can have a hook and loop fastener attached thereto so that the mounting plate 102 can be selectively, removably coupled to the base.

The holding finger 104 can extend away from the longitudinal axis of the mounting plate 102. In one aspect, the holding finger can extend away from the mounting plate at substantially a right angle to the longitudinal axis of the mounting plate 102. Alternatively, the holding finger 104 can extend away from the mounting plate at an acute angle relative to the longitudinal axis of the mounting plate 102. In another aspect, the holding finger can have a longitudinal length configured to position the base 12 of the apparatus at a desired height relative to the user. In a further aspect, the holding finger can be configured for selective attachment to the hook 100. For example, the holding finger can have an inner lumen 108 configured to engage a post 110 of the hook.

Figure 11:
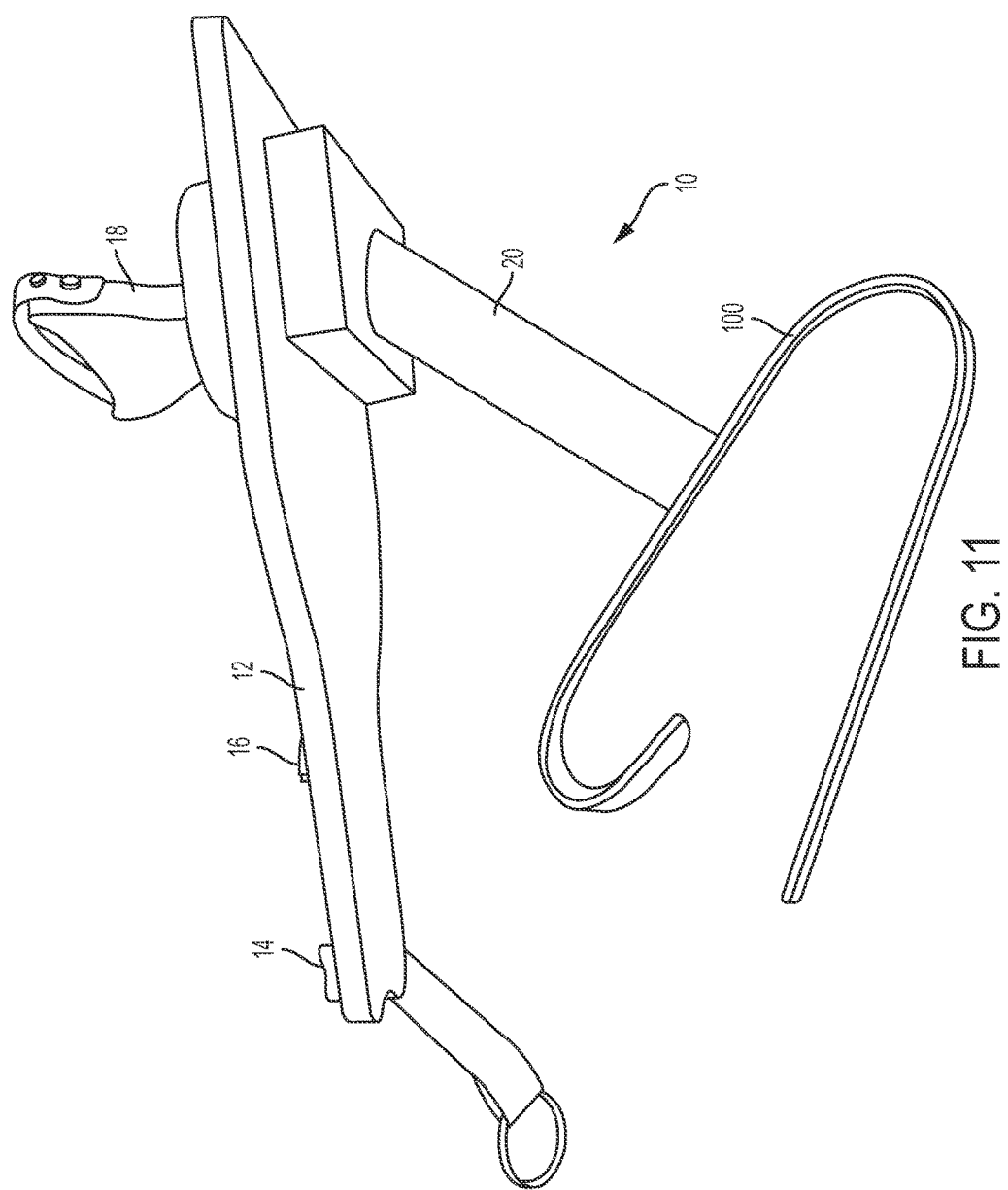
FIG. 11 is a perspective view of a self-catheterization assistance apparatus of the present application showing a base, a flexible penis retention element, a catheter retention member, an advancer, a holder and the hook of FIG. 10 in an assembled position, according to one aspect.
Figure 12:
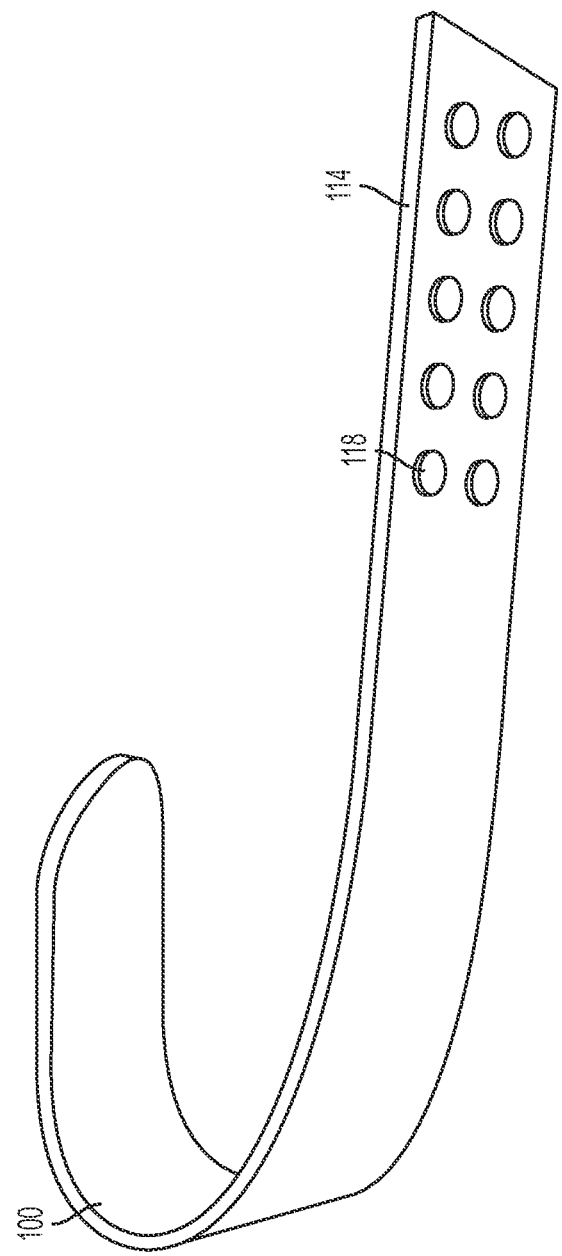
FIG. 12 is a perspective view of a hook of the self-catheterization assistance apparatus of the present application, according to one aspect.

In one aspect, the hook 100 can be configured for selective attachment to a chair and/or bed of the user. For example, the hook 100 can be formed from a conventional "Betty Hook" or pants holder having a "U" or "C"-shape. In this example, the inner portion of the "U" or "C"-shape can engage a portion of the chair and/or bed of the user such that a lower section 112 of the hook 100 is below a portion of the chair and/or bed, and an upper section 114 of the hook 100 is above a portion of the chair and/or bed. In another aspect, the post 110 can extend longitudinally away from the upper section of the hook 100. In one aspect, the post 110 can extend away from the upper section 114 at substantially a right angle to the upper section 114. Alternatively, the post 110 can extend away from the upper section 114 at an acute angle relative to the upper section 114. In another aspect, the post 110 can be configured to matingly engage the holding finger 104. For example, in one aspect, the post 110 can be inserted into the inner lumen 108 of the holding finger 104 so that a proximal end 116 of the holding finger rests against the upper section 114 of the hook 100, as illustrated in FIG. 11.

Figure 13:
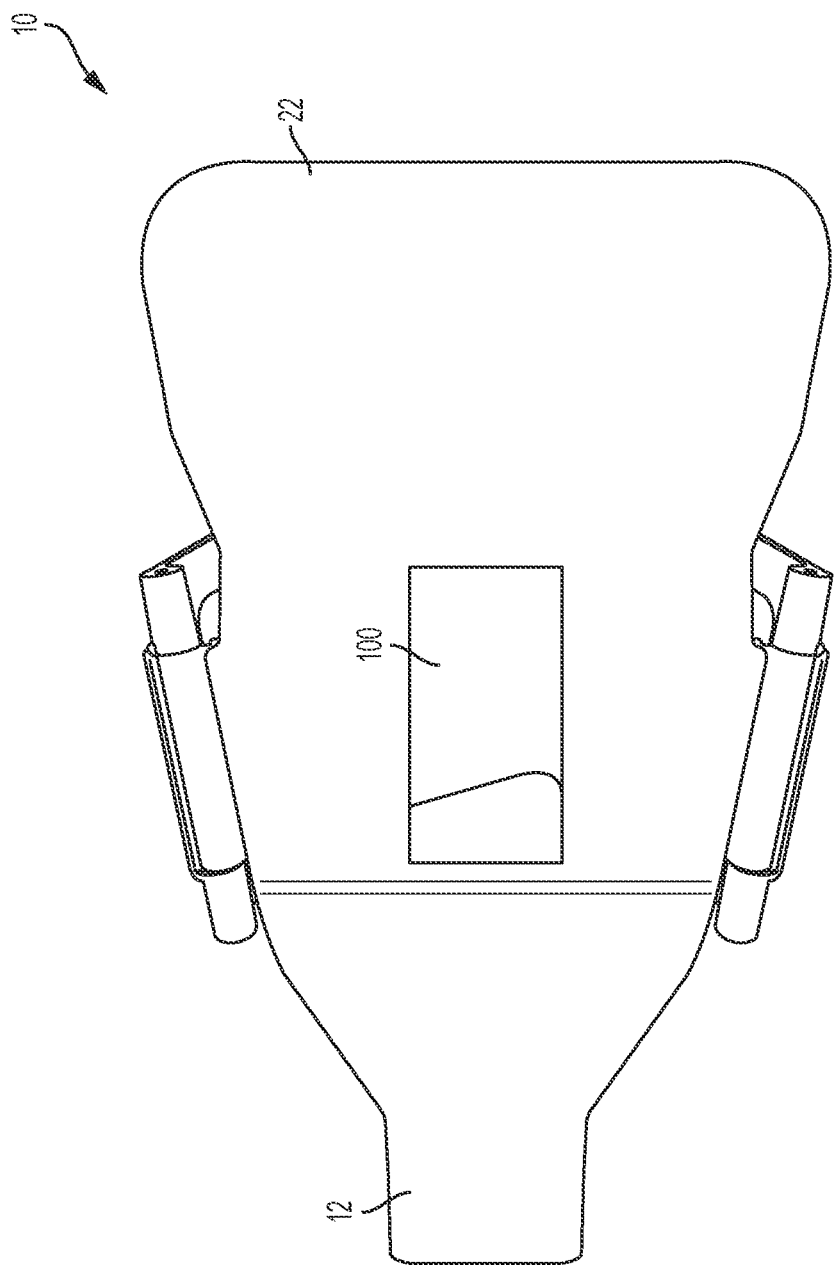
FIG. 13 is a view of the self-catheterization assistance apparatus of the present application showing a base and the hook of FIG. 12 in an assembled position, according to one aspect.

Optionally, in one aspect, the hook 100 can be coupled directly to the lower surface 22 of the base 12 without the holder, as illustrated in FIG. 13. For example and with reference to FIG. 12, a plurality of snaps 118 can be positioned on the upper section 114 of the hook for mating engagement with complementary snaps positioned on the lower surface of the base. In another example, a hook and loop fastener can be used to couple the hook 100 to the lower surface 22 of the base 12. In this example, a hook or a loop portion of the hook and loop fastener can be positioned on the upper section of the hook 100, and a complementary hook or loop portion of the hook and loop fastener can be positioned on the lower surface of the base.

In use, the user can position the base 12 of the self-catheterization assistance apparatus 10 between his legs such that at least a portion of the upper surface 24 of the base 12 is below the penis to be catheterized. Each stabilizer of the plurality of stabilizers 39 can each be rotated to a desired position so that at least a portion of the stabilizers can rest on the top of the legs of the user with the penis in a desired position relative to the base.

Optionally, to support and/or hold the base 12 in the desired position, at least one of the hook 100 and holder 20 can be coupled to the base 12. For example, the hook can engage a portion of the chair or bed of the user such that the lower section 112 of the hook is below a portion of the chair or bed, and the upper section 114 of the hook is above a portion of the chair or bed. The holding finger 104 of the holder can be matingly engaged with the post 110 of the hook 100, and the mounting surface 106 of the mounting plate 102 can be coupled to the lower surface 22 of the base 12. Alternatively, the upper section of the hook 100 can be coupled directly to the lower surface 22 of the base 12. In one aspect, the legs of the user can contact and apply a force to a portion of the first side 28 and the second side 30 of the base 12 to hold the base in place relative to the user.

With the base 12 positioned as desired, the user can insert at least a portion of the penis into the penis retention element 14. If the penis retention element is a selectively adjustable penis retention element 14, the user can adjust the penis retention element to a desired diameter or until a desired pressure is being applied by the penis retention element 14 to the penis. For example, if the penis retention element comprises a hook and loop fastener, the grasping loop 56 can be used to couple the hook portion of the penis retention element to the loop portion of the penis retention element 14.

In one aspect, the user can insert a portion of the catheter 6 into the catheter retention member 16. For example, if the catheter retention member comprises a hook and loop fastener, at least a portion of the catheter housing 8 can be positioned in the catheter housing chamber 48 and the hook portion 58 of the catheter retention member 16 can be positioned above the catheter housing. The hook portion of the catheter retention member can then be coupled to the loop portion 60 of the catheter retention member. In one aspect, the catheter member grasping loop 64 can be used to couple the hook portion of the catheter retention member 16 to the loop portion of the catheter retention member. In another example, if the catheter retention member 16 comprises a frame 62, at least a portion of the catheter housing 8 can be inserted through the gap 63 so that the frame securely holds the catheter housing in the desired position. In the desired position, the catheter housing can be substantially aligned with and spaced a third predetermined distance from the penis.

The catheter can then be urged towards the user. In one aspect, the catheter gripper assembly 5 can be used to urge the catheter 6 from the pouch 9 and towards the user. In another aspect, the catheter gripper assembly can be moved directly by the hand of the user. Optionally, in yet another aspect, the catheter gripper assembly 5 can be positioned in the catheter gripping cavity 78 of the advancer 18 so that the advancer can be used to move the gripper assembly. For example, the slot 68 of the bottom surface 74 of the advancer can engage a portion of the guide rail 66 of the base 12. The hand of the user can be selectively attached to the handle 70 of the advancer and the user can slide the handle longitudinally along the guide rail such that the catheter gripping assembly is urged by the at least one sidewall 79 of the catheter gripping cavity in a desired direction, and in turn, the catheter gripping assembly 5 urges the catheter in the desired direction.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. A self-catheterization assistance apparatus to assist a user of a urinary catheter in advancing the catheter into a penis of the user, the apparatus comprising:
   a base having a proximal edge, an opposed distal edge, a lower surface and an opposed upper surface configured to support at least a portion of the penis and at least a portion of the catheter thereon;
   a plurality of stabilizers extending away from the base a predetermined distance, wherein each stabilizer of the plurality of stabilizers is sized and shaped to assist the user in positioning the apparatus relative to his body;
   a penis retention element defining a penis opening configured for receipt of at least a portion of the penis, wherein the penis retention element is coupled to the upper surface of the base, and wherein the penis retention element is configured to securely attach the penis to the base; and
   a catheter retention member defining a catheter opening configured for receipt of at least a portion of the catheter, wherein the catheter retention member is coupled to the upper surface of the base and is aligned longitudinally with the penis retention element, and wherein the catheter retention member securely attaches a portion of the catheter to the base.

2. The apparatus of claim 1, wherein the penis retention element is spaced from the proximal edge of the base a first predetermined distance, and wherein the catheter retention member is spaced from the proximal edge of the base a second predetermined distance that is greater than the first predetermined distance and the second predetermined distance is selectively adjustable by the user.

3. The apparatus of claim 2, wherein the second predetermined distance is selectively adjustable by the user by sliding longitudinally from the first predetermined distance to the second predetermined distance.

4. The apparatus of claim 1, wherein at least a portion of the base is planar and configured to position a catheter pouch thereon.

5. The apparatus of claim 4, wherein at least a first portion of the base is positioned in a first plane, and a second portion of the base is positioned in a second plane that is at an acute angle relative to the first plane.

6. The apparatus of claim 1, wherein each stabilizer of the plurality of stabilizers is rotatable about and between a first stabilizer position, in which a proximal portion of the stabilizer is substantially parallel to a portion of the upper surface of the base, and a second stabilizer position in which the proximal portion of the stabilizer is substantially normal to the portion of the upper surface of the base.

7. The apparatus of claim 6, wherein each stabilizer of the plurality of stabilizers is fixedly securable in any position about and between the first stabilizer position and the second stabilizer position.

8. The apparatus of claim 1, wherein the penis retention element is a selectively adjustable penis retention element, wherein an inner diameter of the penis opening is selectively adjustable.

9. The apparatus of claim 8, wherein the selectively adjustable penis retention element is formed from a hook and loop fastener.

10. The apparatus of claim 8, wherein the selectively adjustable penis retention element comprises a hinge positioned between a first arm and a second arm, and wherein the second arm is rotatable about and between a closed position, in which a distal end of the second arm is in contact with a portion of a distal end of the first arm, and an open position, in which the distal end of the second arm is spaced from the distal end of the first arm a predetermined distance.

11. The apparatus of claim 10, further comprising a first magnet positioned on a portion of the distal end of the first arm, and a second magnet positioned on a portion of the distal end of the second arm, wherein the first magnet attracts the second magnet to securely attach the distal end of the second arm to the distal end of the first arm to maintain the second arm in the closed position.

12. The apparatus of claim 8, wherein the penis retention element comprises a retention element grasping loop coupled to a portion of the penis retention element, wherein the grasping loop is configured to assist the user in adjusting the penis retention element.

13. The apparatus of claim 1, wherein the catheter retention member is a selectively adjustable penis retention element, wherein an inner diameter of the catheter opening is selectively adjustable.

14. The apparatus of claim 1, wherein the catheter retention member is a rigid member comprising a frame that is substantially c-shaped.

15. The apparatus of claim 14, wherein the frame defines a gap therein so that a portion of the catheter is insertable through the gap and into the catheter opening.

16. The apparatus of claim 14, wherein the frame is spaced from the upper surface of the base a predetermined frame height.

17. The apparatus of claim 16, wherein the frame height is selectively adjustable.

18. A self-catheterization assistance system comprising:
a urinary catheter; and
a self-catheterization assistance apparatus comprising:
a base having a proximal edge, an opposed distal edge, a lower surface and an opposed upper surface configured to support at least a portion of a penis of a user and at least a portion of the urinary catheter thereon;
a plurality of stabilizers extending away from the base a predetermined distance, wherein each stabilizer of the plurality of stabilizers is sized and shaped to assist the user in positioning the apparatus with his legs;
a penis retention element defining a penis opening configured for receipt of at least a portion of the penis, wherein the penis retention element is coupled to the upper surface of the base, and wherein the penis retention element is configured to securely attach the penis to the base; and
a catheter retention member defining a catheter opening configured for receipt of at least a portion of the catheter, wherein the catheter retention member is coupled to the upper surface of the base and is aligned longitudinally with the penis retention element, and wherein the catheter retention member securely attaches a portion of the catheter to the base.

19. A method for self-catheterization comprising:
providing a urinary catheter and a self-catheterization assistance apparatus comprising:
a base having a proximal edge, an opposed distal edge, a lower surface and an opposed upper surface configured to support at least a portion of the penis and at least a portion of the catheter thereon;
a plurality of stabilizers extending away from the base a predetermined distance, wherein each stabilizer of the plurality of stabilizers is sized and shaped to assist the user in positioning the apparatus relative to his body;
a penis retention element defining a penis opening configured for receipt of at least a portion of the penis, wherein the penis retention element is coupled to the upper surface of the base, and wherein the penis retention element is configured to securely attach the penis to the base; and
a catheter retention member defining a catheter opening configured for receipt of at least a portion of the catheter, wherein the catheter retention member is coupled to the upper surface of the base and is substantially aligned longitudinally with the penis retention element, and wherein the catheter retention member securely attaches a portion of the catheter to the base;
positioning the base on the legs of the user;
inserting a penis through the penis opening of the penis retention element;
inserting a portion of the catheter into the catheter opening of the catheter retention member; and
advancing a portion of the catheter into the penis.

20. A self-catheterization assistance apparatus to assist a user of a urinary catheter in advancing the catheter into a penis of the user, the apparatus comprising:
a base having a lower surface and an opposed upper surface;
a penis retention member attached to the upper surface of said base and configured for releasably securing said user's penis thereto; and
a catheter retention member attached to the upper surface of said base and configured for releasably securing a urinary catheter thereto;
wherein the penis retention member is spaced from the catheter retention member by a predetermined distance, and wherein the predetermined distance is selectively adjustable by the user.

21. The apparatus of claim 20, wherein said upper surface comprises a first portion having a first plane and a second portion having a second plane, wherein said penis retention member is positioned in said first plane and second plane is at an acute angle relative to the first plane and configured so urine flows downwardly from the first plane.

22. The apparatus of claim 20, further comprising at least one body stabilizer extending away from the base and configured to rest on top of a leg of the user.

* * * * *